United States Patent [19]

Larsen et al.

[11] Patent Number: 5,723,476
[45] Date of Patent: Mar. 3, 1998

[54] 4-HYDROXYCOUMARIN-3-CARBOXAMIDES FOR THE TREATMENT OF DIABETES MELLITUS

[75] Inventors: Scott D. Larsen; Jerry R. Colca, both of Kalamazoo; Peter K. W. Harris, Portage; Howard R. Miller; Alice L. Laborde, both of Kalamazoo; Rolf F. Kletzien, Plainwell; Heinrich Josef Schostarez, Portage, all of Mich.

[73] Assignee: Pharmacia & Upjohn Company, Kalamazoo, Mich.

[21] Appl. No.: 747,185

[22] Filed: Nov. 12, 1996

Related U.S. Application Data

[60] Provisional application No. 60/006,878, Nov. 17, 1995 and Provisional application No. 60/019,976, Jun. 17, 1996.

[51] Int. Cl.[6] ............................ A61K 31/35; A61K 31/37
[52] U.S. Cl. .................... 514/337; 514/359; 514/362; 514/363; 514/444
[58] Field of Search ........................ 514/454, 457, 514/362, 363, 337, 444, 359

[56] References Cited

U.S. PATENT DOCUMENTS

| | | | |
|---|---|---|---|
| 3,122,557 | 2/1964 | Molho et al. | 260/295 |
| 4,078,075 | 3/1978 | Beriger | 424/281 |
| 4,210,667 | 7/1980 | Sarges et al. | 424/281 |
| 4,766,144 | 8/1988 | Müller et al. | 514/457 |
| 5,412,104 | 5/1995 | Afonso et al. | 548/525 |
| 5,514,706 | 5/1996 | Ambler et al. | 514/454 |
| 5,554,611 | 9/1996 | Schonafinger et al. | 514/228.2 |

FOREIGN PATENT DOCUMENTS

| | | |
|---|---|---|
| 241834 | of 0000 | European Pat. Off. |
| 4667 | of 0000 | Japan |
| 92/04327 | of 0000 | WIPO |
| WO 92/06083 | 4/1992 | WIPO |
| WO 94/05649 | 3/1994 | WIPO |

*Primary Examiner*—Mukund J. Shah
*Assistant Examiner*—Bruck Kifle
*Attorney, Agent, or Firm*—Lucy X. Yang

[57] ABSTRACT

The present invention provides some novel 4-hydroxycoumarin-3-carboxamide derivatives and the use of a broad class of 4-hydroxycoumarin-3-carboxamide derivatives for the treatment of a patient suffering from or susceptible to diabetes mellitus.

8 Claims, 1 Drawing Sheet

FIGURE 1

Effect of compound No. 4 on Isolated Adipocytes Glucose Inco Incorporation

FIGURE 2

Effect of compound No. 4 on KKAy Mice Reduction in Blood Glucose

4-HYDROXYCOUMARIN-3-CARBOXAMIDES FOR THE TREATMENT OF DIABETES MELLITUS

CROSS-REFERENCE TO RELATED APPLICATION

This application claims the benefit of the following provisional applications: U.S. Ser. No. 60/006,878, filed Nov. 17, 1995, and U.S. Ser. No. 60/019,976, filed Jun. 17, 1996, under 35 U.S.C 119(e)(i).

FIELD OF THE INVENTION

The present invention relates to 4-hydroxycoumarin-3-carboxamides. More particularly, the present invention relates to novel 4-hydroxycoumarin-3-carboxamides having formulas IA, IB and IC, and the use of 4-hydroxycoumarin-3-carboxamides having formula I for the treatment of diabetes mellitus.

BACKGROUND OF THE INVENTION

Diabetes mellitus is a clinical syndrome characterized by inappropriate hyperglycemia caused by deficiency of insulin or by a resistance to the action of insulin (insulin insensitive). It is the most common endocrine disorder, affecting approximately 12 million individuals in the United States, and perhaps as many as 200 million worldwide.

Resistance to the action of insulin is a common phenomenon and plays a central role in the pathogenesis and clinical course of several important human diseases. The fact that a large number of patients with diabetes are "insulin insensitive" was first demonstrated about 60 years ago. It was suggested that patients with diabetes should be divided into two categories, insulin sensitive and insulin insensitive. This point of view became institutionalized when the National Diabetes Data Group came to the same conclusion, about 40 years after the original observations, and we now use the terms insulin dependent diabetes mellitus (IDDM) and non-insulin dependent diabetes mellitus (NIDDM).

IDDM, generally referred to as Type I diabetes, is a disease of disordered immune function, involving the destruction of pancreatic β-cells that produce insulin. The onset of clinical symptoms of Type I diabetes represents the end point of a chronic progressive decline in β-cell function, and occurs when the majority of β-cells have been lost which leads to absolute dependence on exogenous insulin.

Type II, or NIDDM, diabetes is a very distinct disorder as compared with IDDM. NIDDM classically develops in an older patient population and may or may not require the use of therapeutic insulin. NIDDM is characterized by glucose intolerance and an impairment in tissue sensitivity to the action of insulin, i.e., a resistance to insulin-mediated glucose uptake by muscle. A two-step model for development of NIDDM has been proposed. Saad, M. F. et al., Am. J. Med., vol. 90, pp 229-35 (1991). The first step is development of impaired glucose tolerance, which depends on the occurrence of, and is determined primarily by, insulin resistance. The second step is the transition from impaired glucose tolerance to NIDDM that is accompanied by some further worsening of insulin resistance, with primary or secondary β-dysfunction playing some critical roles during deterioration from impaired glucose tolerance to NIDDM.

In Type I diabetes the primary alteration resides in the pancreas, resulting in insulin deficiency, whereas in Type II diabetes, the underlying resistance of the tissues to insulin may exist for many years before the diagnosis of diabetes is made. Thus, although the characteristics of Type I and Type II diabetes are very different, both could be treated by an agent which is able to either work like insulin or augment the activity of insulin.

Compounds of formula I of the present invention have been discovered as agents capable of enhancing autophosphorylation of the insulin receptor, a necessary first step in the activity of insulin. The compounds improve the sensitivity of peripheral tissues to the action of insulin, i.e., insulin-mediated glucose uptake by muscle and therefore they are useful in the treatment of NIDDM. Compounds of formula I also demonstrate some effects on glucose incorporation in isolated cell in the absence of insulin. Therefore, they are beneficial in the treatment of IDDM.

INFORMATION DISCLOSURE

International Publication No. WO92/06083 discloses 3-carbamoyl-4-hydroxy-coumarin derivatives useful as antiparasitic agents, e.g., antihelminthic and anticoccidial agents.

International Publication No. WO92/04327 discloses heterocyclic compounds useful as antihypertensive agents and useful as antiviral agents against DNA-containing viruses, such as herpes group viruses.

International Publication No. WO94/05649 discloses 3-phenylcarbamoyl-4-hydroxy-coumarin derivatives useful as broad-spectrum antibacterial agents, especially active against Gram-positive bacteria.

European Patent Publication 241,834 discloses 3-aryl:carbamoyl-4-hydroxy-coumarin derivatives useful as anthelmintics.

Derwent Abstracts 16517X/09 discloses helminth control with substituted benzopyran-3-carboxyanilides.

U.S. Pat. No. 3,122,557 discloses coumarin, α-pyrone-3-carboxyamides useful as antifungals and antibacterials.

Japanese Patent 4667 (Feb. 25, 1967) discloses N-substituted 3-carbamoyl-4, hydroxycoumarins useful as antibacterials.

SUMMARY OF THE INVENTION

The present invention provides a method of treating a patient suffering from or susceptible to diabetes mellitus by administering an effective amount of a compound of formula I or pharmaceutically acceptable salts thereof wherein:

$R_1$ is (a) H, (b) F, (c) Cl, or (d) $CH_3$;

$R_2$ is (a) H, (b) F, (c) Cl, (d) Br, or

(e) Phenyl;

3 or $R_1$ and $R_2$ taken together is phenyl;

$R_3$ is
(a) H,
(b) Cl,
(c) F,
(d) —NO$_2$,
(e) phenoxy,
(f) Br, or
(g) CF$_3$;

$R_4$ is
(a) 3-carbamoyl-5-methylthien-2-yl,
(b) 5-(trifluoromethyl)-1,3,4-triazol, $R_5$ is
(a) H, or
(b) Cl;

$R_6$ is
(a) H,
(b) Br,
(c) F,
(d) benzoyl,
(e) 5-trifluoromethyl-1,3,4-thiadiazol-2-oxy, or
(f) (CH$_3$)CH—P—O(OEt$_2$);

$R_7$ is
(a) —SO$_2$CH$_3$,
(b) —SO$_2$NH$_2$,
(c) —SO$_2$N(CH$_3$)$_2$,
(d) CF$_3$,
(e) CF$_2$Cl,
(f) CF$_2$H,
(g) Br,
(h) Cl, or
(i) CF$_2$CF$_3$;

$R_8$ is
(a) H, or
(b) Cl; and $R_9$ is
(a) Br, or
(b) CF$_3$.

The invention also includes compounds of formulas IA, IB, IC:

or pharmaceutically acceptable salts thereof wherein $R_{10}$ is
a) H, or
b) Cl;

$R_{11}$ is
a) H,
b) phenyl,
c) Cl,
d) F, or
e) Br;

$R_{12}$ is
a) H,
b) CH$_3$,
c) Cl, or
d) F;

or $R_{11}$ and $R_{12}$ taken together is phenyl;

$R_{13}$ is
a) 5-bromopyridin-2-yl,
b) 5-(trifluoromethyl)-1,3,4-thiadiazol-2-yl,
c) 4-bromophenyl,
d) 5-(difluoromethyl)-1,3,4-thiadiazole-2-yl,
e) 5-(pentafluoroethyl)1,3,4-thiadiazole-2-yl, or
f) 5-(difluorochloromethyl)-1,3,4-thiadiazole-2-yl;

and with the following provisos:
a) when $R_{10}$ is H, at least one of $R_{11}$ or $R_{12}$ is other than H,
b) when $R_{10}$ is Cl, $R_{11}$ is Cl, and $R_{12}$ is 4-bromophenyl;

wherein
$R_{14}$ is
a) H,
b) Cl, or
c) NO$_2$;

$R_{15}$ is
a) 3-carbamoyl-5-methylthien-2-yl,
b) 4-bromophenyl,
c) 5-(trifluoromethyl)-1,3,4-triazol-2-yl,
d) 4-[5-(trifluoromethyl)-1,3,4-thiadiazol-2-yloxy] phenyl, or
e) 4-benzoylphenyl;

and with the following provisos:
a) when $R_{14}$ is H, $R_{15}$ is 3-carbamoyl-5-methylthien-2-yl or 4-[5-(trifluoromethyl)-1,3,4-thiadiazol-2-yloxy] phenyl, b) when $R_{14}$ is Cl, $R_{15}$ is 4-benzoylphenyl or 5-(trifluoromethyl)-1,3,4-triazol-2-yl, or c) when $R_{14}$ is —$NO_2$, $R_{15}$ is 4-bromophenyl;

wherein $R_{16}$ is a) F, b) Cl, c) Br, d) $CF_3$, or e) phenoxy;

$R_{17}$ is a) $CF_2H$, c) $CF_3$ b) $SO_2CH_3$, c) $SO_2NH_2$, or d) $SO_2N(CH_3)_2$;

and with the following provisos:

a) when $R_{17}$ is $SO_2CH_3$, $SO_2NH_2$, or $SO_2N(CH_3)_2$, $R_{16}$ is Cl, b) when $R_{17}$ is $CF_3$, $R_{16}$ is phenoxy, or c) when $R_{17}$ is $CF_2H$, $R_{16}$ is F, Cl, Br, or $CF_3$.

Compounds of formulas I, IA, IB, and IC of the present invention have been discovered as agents capable of enhancing autophosphorylation of the insulin receptor, a necessary first step in the activity of insulin. The compounds improve the sensitivity of peripheral tissues to the action of insulin, i.e. insulin mediated glucose uptake by muscle and therefore they are useful in the treatment of NIDDM. Compounds of formula I also demonstrate some effects on glucose incorporation in isolated cell in the absence of insulin. Therefore, they are beneficial in the treatment of IDDM.

DETAILED DESCRIPTION OF THE INVENTION

The present invention provides some novel 4-hydroxycoumarin-3-carboxamide derivatives and the use of a broad class of 4-hydroxycoumarin-3-carboxamide derivatives for the treatment of diabetes mellitus, i.e., insulin dependent diabetes mellitus (IDDM) and non-insulin dependent diabetes mellitus (NIDDM).

NIDDM is characterized by glucose intolerance and an impairment in tissue sensitivity to the action of insulin. Insulin action is exerted through a specific cellular receptor for hormone. The insulin receptor directs the insulin to a specific target tissue and programs the response of the tissue to the insulin. The insulin receptor transmitting its signal involves a phosphorylation cascade, i.e., insulin induces receptor autophosphorylation, which activates the receptor kinase, which in turn phosphorylates one or more cellular substrates. These substrates could be enzymes (serine kinases or phosphoprotein phosphatases) or enzyme inhibitors whose activity is changed by these phosphorylation and dephosphorylation reactions. In most cases, reduced sensitivity of cells to insulin is not due to mutations in the receptor itself, but rather results from attenuation of the insulin signaling pathway with the defect apparent at the receptor level. Thus, compounds that can increase receptor autophosphorylation would augment insulin signal transduction. Compounds of formula I of the present invention have been detected by ELISA technology capable of enhancing autophosphorylation of the insulin receptor, a necessary first step in the insulin-signaling cascade. Compounds identified from this test have also demonstrated increased glucose uptake in the presence and absence of insulin in vitro. Also, compounds of formula I have been administered to KKAy mice, rodent models of Type II diabetes, and demonstrate the reduction of glucose concentration, indicating improved glucose tolerance. Therefore, the compounds are useful in the treatment of NIDDM.

IDDM is characterized by inappropriate hyperglycemia caused by deficiency of insulin. The patients experiencing IDDM require the administration of insulin for survival. Therefore, an agent which is able to work like insulin is beneficial in treating IDDM. As stated above, compounds of formula I demonstrate some effects on glucose uptake in isolated cell in the absence of insulin. As such, it is reasonable to expect that compounds could also be used either as an adjunctive or alternative therapy for the treatment of IDDM.

Table 1 contains a list of compounds being claimed for use in the treatment of diabetes mellitus and provides a summary of the increase in insulin receptor autophosphorylation induced by the corresponding compounds of the present invention. Results in Table 1 are presented as percentages of insulin receptor phosphotyrosine content in compound-treated cell lysates relative to untreated controls, both of which were incubated in the presence of 2 nM insulin. Thus, for example, cells incubated with compound No. 4 and 2 nM insulin induced the phosphotyrosine content of the insulin receptor to increase to a level 3.27 times higher than cells incubated with 2 nM insulin alone (327%). In this assay, a value of 150% is the minimum necessary for a compound to be considered active at increasing the response of the insulin receptor to insulin. Results in Table 1 are compiled under the heading "% of 2 nM insulin response".

Figure 1:
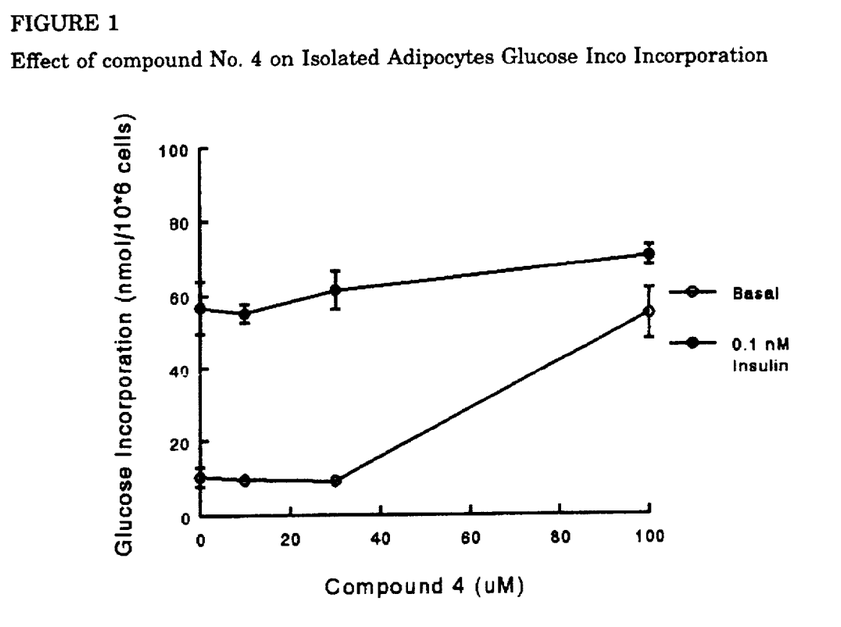

FIG. 1 illustrates the effect of 7-chloro-4-hydroxy-3-[N-[5-bromo-1,3,4-thiadiazol-2-yl]carbamoyl]-coumarin (compound No. 4) on isolated adipocytes. The data demonstrate that the compound increases glucose uptake in the presence and absence of insulin.

Figure 2:
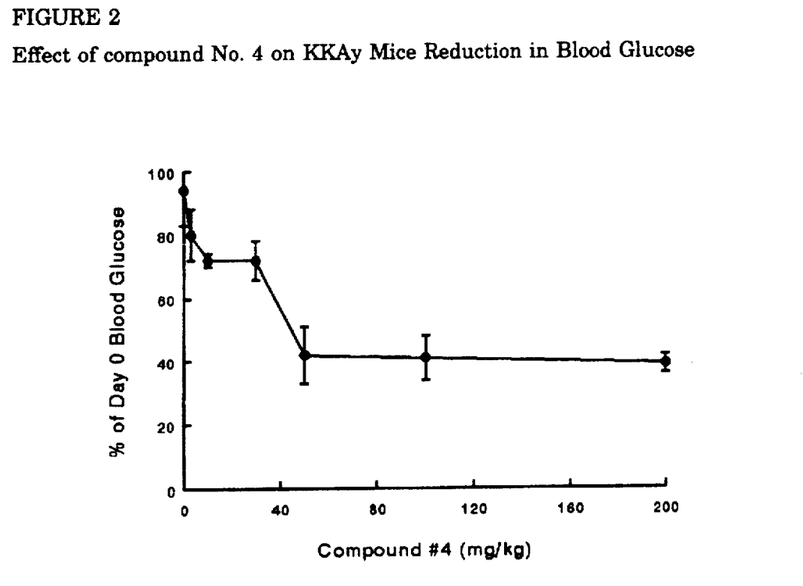

FIG. 2 illustrates the effect of 7-chloro-4-hydroxy-3-[N-[5-bromo-1,3,4-thiadiazol-2-yl]carbamoyl]-coumarin (compound No. 4) in KKAy mice. Administration of the compound of this invention to KKAy mice at a dose of approximately 0.1–200 mg/kg of body weight per day for 3 days decreased the blood glucose level in this rodent model of non-insulin dependent diabetes mellitus. A dose of 40 mg/kg of body weight/day produced a 45% decrease in the blood glucose level. Higher doses produced greater reductions in the blood glucose concentration. However, administration of compounds at higher than 100 mg/kg/day produced an approximately similar reduction in blood glucose concentration as achieved at 70 mg/kg/day. Therefore, the dose of compounds of formula I to be used is between 0.1 and 100 mg/kg body weight daily. The preferred dose is 0.1–50 mg/kg/day. KKAy mice are insulin resistant and the finding that the non-fasting blood glucose level is reduced in these animals indicates that insulin resistance is most probably less after treatment with the claimed compounds.

By a patient suffering from or susceptible to diabetic mellitus is meant a human having inappropriate hyperglycemia caused by deficiency of insulin or by a resistance to the action of insulin (insulin insensitive). By treating is meant a decrease in, or partial or total avoidance of, inappropriate hyperglycemia in a patient. Such patients are readily diagnosed by a physician of ordinary skill.

The compounds of formulas I, IA, IB, and IC of this invention may be prepared according to the procedures described in International Publication No. WO 92/06083, International Publication No. WO 94/05649, Japanese Patent 4668, U.S. Pat. No. 3,122,557, U.S. Pat. No. 3,726,892, Swiss Patent 513585, and *J. Chem. Soc.* p. 1508 (1958). Scheme I illustrates a general method for the preparation of compounds of formulas IA, IB, and IC. Example I provides a detailed description for the preparation of compounds of formulas IA, IB, and IC.

The compounds of formula I can also be in pharmaceutically acceptable salt form in the treatment of diabetes mellitus. The term "pharmaceutically acceptable salts" refers to salts useful for administering the compounds of this invention and these include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate. These salts may be in hydrated form. Some of the compounds of this invention may form metal salts such as: sodium, potassium, calcium and magnesium salts and these are embraced by the term "pharmaceutically acceptable salts."

The compounds of this invention can be administered to humans in any number of conventional dosage form, e.g., oral, rectal, parenteral, topical, transdermal, inhalation and the like. Oral or rectal dosage forms include capsules, tablets, pills, powder, cachets, and suppositories. Liquid oral dosage forms include solutions and suspensions. Parenteral preparations include sterile solutions and suspensions. Inhalation administration can be in the form of a nasal, oral spray, or by insufflation. Topical dosage forms can be creams, ointments, lotions, transdermal devices (e.g., of the conventional patch or matrix type) and the like. In general, the preferred form of administration is orally.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives, lubricants, etc.

BIOLOGICAL TESTING

Compounds of the present invention were tested for their ability to increase insulin receptor autophosphorylation, to improve glucose incorporation in vitro in the presence and absence of insulin, and to reduce blood glucose in vivo. The present invention is seen more fully by the procedures given below.

Procedure 1

Increase of Insulin Receptor Autophosphorylation

Insulin signaling is accomplished via a phosphorylation cascade which is initiated at the receptor following interaction with insulin; therefore, compounds that can increase receptor autophosphorylation would augment insulin signal transduction. To demonstrate the increase of insulin receptor autophosphorylation induced by the compounds of the present invention, an assay to monitor the tyrosyl phosphorylation state of the insulin receptor has been developed. A CHO cell line stably transfected with an expression plasmid encoding the human insulin receptor is inoculated into 96 well dishes. Following exposure of cells to 2 nM dose of insulin and 100 μm the testing compounds, a post-nuclear lysate is prepared by detergent lysis. The lysates are added to 96 well dishes which have been coated with the plant lectin, lens culinaris agglutinin, which binds to the insulin receptor. Following washing, the phosphorylation state of the insulin receptor is monitored by a mouse antiphosphotyrosine antibody coupled to a goat anti-mouse antibody conjugated to horse radish peroxidase. Quantification of the reaction is determined by reading absorbance at 450 nM. Table 1 contains a list of compounds being claimed for use in the treatment of diabetes mellitus and provides a summary of the increase in insulin receptor autophosphorylation induced by the corresponding compounds of the present invention. These compounds all substantially increased the ability of insulin to stimulate the phosphotyrosine content of the insulin receptor as demonstrated in the lysates of cells incubated in the combined presence of the compound and a submaximal dose of insulin (2 nM). Results in Table 1 are presented as percentages of insulin receptor phosphotyrosine content in compound-treated cell lysates relative to untreated controls, both of which were incubated in the presence of 2 nM insulin.

Procedure 2

Improvement of Glucose Incorporation in Isolated Adipocytes

To demonstrate the improvement of glucose uptake in vitro, rat adipocytes were isolated from the epididymal fat pad and incubated with the 0–100 uM concentration of 7-chloro-4-hydroxy-3-[N-[5-bromo-1,3,4-thiadiazol-2-yl]carbamoyl]-coumarin (compound No. 4) for 15 minutes prior to a 5 minute exposure to 0.1 nM insulin. Within a 30 minute period the incorporation of 6–3 H-glucose was measured by the procedure described in McCroskey et al., Biochem. Biophys. Acta, vol. 1011, pp 212–219 (1989). In addition, a parallel assay was conducted without exposuring to insulin (Basal). As shown in FIG. 1, the compound increases glucose uptake in the presence and absence of insulin Procedure 3

Reduction of Blood Glucose in KKAy Mice

To test the effect of compounds of formula I on blood glucose in KKAy mice, the mice are administered 7-chloro-4-hydroxy-3-[N-[5-bromo-1,3,4-thiadiazol-2-yl]carbamoyl]-coumarin (compound No. 4) in rodent chow. KKAy mice are rodent models of NIDDM. A pretreatment blood sample was obtained from the retro-orbital sinus and the mice arranged in groups of 6 so that the mean pretreatment blood glucose level was the same on average in all groups. Testing compounds were admixed in the chow so as to achieve the daily dosages at concentration of 50–200 mg; mice were allowed to consume the diet ad libitum. Control mice received unsupplemented chow. On Day 0, the mice provided control chow or chow supplemented with testing compounds. After 3 days of consuming control chow or chow supplemented with test compounds, a blood sample was collected and plasma analyzed for determination of the glucose concentration. Food consumption was measured by weighing the food provided at the beginning of the study and the food residue at the end of the study. Food consumption was calculated by subtracting the weight of the residue from the weight of the food provided. Drug intake was calculated from the food content of compound and total food intake. Administration of the compound of this invention to KKAy mice at a dose of approximately 0.1–200 mg/kg of body weight per day for 3 days decreased the blood glucose level in those rodent models of non-insulin dependent diabetes mellitus. A dose of 40 mg/kg of body weight/day produced a 45% decrease in the blood glucose level. Higher doses produced greater reductions in the blood glucose concentration. However, administration of compounds at higher than 100 mg/kg/day produced an approximately similar reduction in blood glucose concentration as achieved at 70 mg/kg/day. Therefore, using this method significant blood glucose lowering in KKAy mice occurred at doses from 10–50 mg/kg/day. Based on experience, it is expected that doses in man may be 5–10 times less as compared to mice. Blood glucose data are expressed as the average blood glucose concentration in the testing group. The results are summarized in FIG. 2.

EXAMPLE 1

Preparation of 6-chloro-4-hydroxy-3-[N-[5-(trifluoromethyl)-1,3,4-thiadiazole-2-yl]carbamoyl] coumarin Step 1
Preparation of 2H-1-benzopyran-3-carboxylic acid, 6-chloro-4-hydroxy-2-oxo, ethyl ester.

To a suspension of magnesium ethoxide (4.56 g, 39.8 mmol) in toluene (30 mL) in a flame-dried flask under nitrogen is added diethyl malonate (6.5 mL, 43.2 mmol). The resulting suspension is stirred at ambient temperature for 3 hours, then cooled to 0° C. In a separate flask, a suspension of 6-fluorosalicylic acid (5.19 g, 33.2 mmol) in toluene (100 mL) is cooled to 0° C. Triethylamine (9.3 mL, 66.5 mmol) is added to achieve a clear solution. Ethyl chloroformate (6.7 mL, 69.7 mmol) is added slowly such that the reaction temperature is not allowed to exceed 10° C. After stirring further for one hour at 0° C., the diethyl malonate solution is added over several portions such that the reaction temperature does not exceed 10° C. The reaction is stirred at 0° C. for another hour, then allowed to attain ambient temperature and stir overnight. The reaction is diluted with 100 mL of toluene, quenched with HCl (3M aqueous) and allowed to stir 30 minutes. The organic phase is partitioned and washed with 3M aqueous HCl, $H_2O$, saturated aqueous $NaHCO_3$, and $H_2O$. The organic phase is concentrated to a yellow oil, which is dissolved in aqueous NaOH (3M) and allowed to stand. The resulting precipitate is collected, acidified with aqueous citric acid (1M), and extracted into $CH_2Cl_2$ (4×125 mL). Drying over $MgSO_4$, filtration, and concentration in vacuo yields a crude beige solid, which is recrystallized in ethyl acetate to provide the title compound as a white solid.

$^1$H NMR ($CDCl_3$) d 1.45, 4.50, 7.24, 7.59, 7.95, 14.73.

Step 2.
Preparation of 6-chloro-4-hydroxy-3-[N-[5-(trifluoromethyl)-1,3,4-thiadiazole-2-yl]carbamoyl] coumarin.

To a suspension of 2H-1-benzopyran-3-carboxylic acid, 6-chloro-4-hydroxy-2-oxo, ethyl ester (1.01 g, 3.76 mmol) in xylene (10 mL) is added 2-amino-5-trifluoromethyl-1,3,4-thiadiazole (636 mg, 3.76 mmol). The resulting suspension is heated to reflux and stirred at that temperature overnight. After cooling to room temperature, the resulting precipitate is collected, washed well with methanol, and dried to provide the title compound as a solid.

$^1$H NMR (DMSO-$d_6$) d 7.23, 7.59, 7.87, 11.79, 14.98.

Following the general procedure of EXAMPLE 1, the following novel coumarin amides are prepared.

Coumarin, 4-hydroxy-6-phenyl-3-[N-(5-bromopyridin-2-yl)carbamoyl]-
mp 273.5° C.;

Coumarin, 3-[N-(3-carbamoyl-5-methylthien-2-yl)carbamoyl]-4-hydroxy-
mp 283°–285° C.;

Coumarin, 6-fluoro-4-hydroxy-3-[N-[5-(trifluoromethyl)-1,3,4-thiadiazol-2-yl]-carbamoyl]-
mp 264.8° C.;

Coumarin, 4-hydroxy-7-nitro-3-[N-(4-bromophenyl)carbamoyl]-
mp 277° C.;

Coumarin, 4-hydroxy-5-methyl-3-[N-(4-bromophenyl)carbamoyl]-
mp 197.3° C.;

Coumarin, 5-chloro-4-hydroxy-3-[N-(4-bromophenyl)carbamoyl]-
mp 236.2° C.;

Coumarin, 5-chloro-4-hydroxy-3-[N-[5-(trifluoromethyl)-1,3,4-thiadiazol-2-yl]carbamoyl]-
mp 260.7° C.;

Coumarin, 7-chloro-4-hydroxy-3-[N-[5-(trifluoromethyl)-1,3,4-triazol-2-yl]carbamoyl]-
mp 261.2° C.;

Coumarin, 4-hydroxy-3-[N-(4-(5-(trifluoromethyl)-1,3,4-thiadiazol-2-yloxy)phenyl)-carbamoyl]-
mp 236.5° C.;

Coumarin, 7-chloro-4-hydroxy-3-[N-(4-benzoyl-phenyl)carbamoyl]-
mp 242°–246° C.;

Coumarin, 7-bromo-4-hydroxy-3-[N-[5-(difluoromethyl)-1,3,4-thiadiazol-2-yl]carbamoyl]-
mp 254.5° C.;

Coumarin, 6,7-dichloro-4-hydroxy-3-[N-(4-bromophenyl)carbamoyl]-
mp 256°–258° C.;

Coumarin, 7-trifluoromethyl-4-hydroxy-3-[N-[5-(difluoromethyl)-1,3,4-thiadiazole-2-yl]carbamoyl]-
mp 268°–270 ° C.;

3H-Naptho[2,1-b]pyran-3-one, 1-hydroxy-2-[N-[5-(trifluoromethyl)-1,3,4-thiadiazole-2-yl]carbamoyl]-
mp 264°–265° C.;

Coumarin, 5-fluoro-4-hydroxy-3-[N-[5-(trifluoromethyl)-1,3,4-thiadiazole-2-yl]carbamoyl]-
mp 264°–265° C.;

Coumarin, 5-fluoro-4-hydroxy-3-[N-[5-(difluoromethyl)-1,3,4-thiadiazole-2-yl]carbamoyl]-
mp 224°–225° C.;

Coumarin, 6-fluoro-4-hydroxy-3-[N-[5-(difluoromethyl)-1,3,4-thiadiazole-2-3-yl]carbamoyl]-
mp 224°–225° C.;

Coumarin, 5-fluoro-4-hydroxy-3-[N-[5-(pentafluoroethyl)-1,3,4-thiadiazole-2-yl]carbamoyl]-
mp 240°–242° C.;

Coumarin, 5-fluoro-4-hydroxy-3-[N-[5-(difluorochloromethyl)-1,3,4-thiadiazole-2-yl]carbamoyl]-
mp 243°–244° C.;

Coumarin, 6-bromo-4-hydroxy-3-[N-[5-(difluorochloromethyl)-1,3,4-thiadiazole-2-yl]carbamoyl]-
mp 227°–228° C.;

Coumarin, 6-chloro-4-hydroxy-3-[N-[5-(difluoromethyl)-1,3,4-thiadiazole-2-yl]carbamoyl]-
mp 238°–240° C.;

Coumarin, 7-chloro-4-hydroxy-3-[N-[5-(difluoromethyl)-1,3,4-thiadiazol-2-yl]carbamoyl]-
$^1$H NMR (DMSO-$d_6$) d 7.29, 7.37, 7.44, 7.91, 10.68, 14.31;

Coumarin, 7-fluoro-4-hydroxy-3-[N-[5-(difluoromethyl)-1,3,4-thiadiazole-2-yl]carbamoyl]-
$^1$H NMR (DMSO) δ 7.08–7.16, 7.43, 8.00, 14.74;

Coumarin, 7-chloro-4-hydroxy-3-[N-[5-(methylsulfonyl)-1,3,4-thiadiazol-2-yl]carbamoyl]-
m.p. 293°–294° C.;

Coumarin, 7-chloro-4-hydroxy-3-[N-[5-(aminosulfonyl)-1,3,4-thiadiazole-2-yl]carbamoyl]-
m.p. 267°–269° C.;

Coumarin, 4-hydroxy-7-phenoxy-3-[N-[5-(trifluoromethyl)-1,3,4-thiadiazol-2-yl]carbamoyl]-
mp 250°–253° C.;

Coumarin, 7-chloro-4-hydroxy-3-[N-[5-(dimethylaminosulfonyl)-1,3,4-thiadiazole-2-yl]carbamoyl]-
m.p. 273°–276° C.

SCHEME I

TABLE 1

| | Increase of Insulin Receptor Autophosphorylation | | |
|---|---|---|---|
| Compound No. | Structure | Compound Name | % of 2 nM insulin response |
| 1 | (structure) | Coumarin, 4-hydroxy-6-phenyl-3-[N-(5-bromopyridin-2-yl)carbamoyl]- | 151 |
| 2 | (structure) | Coumarin, 7-chloro-4-hydroxy-3-[N-[5-(methylsulfonyl)-1,3,4-thiadiazol-2-yl]-carbamoyl]- | 232 |
| 3 | (structure) | Coumarin, 7-chloro-4-hydroxy-3-[N-[5-(trifluoromethyl)-1,3,4-thiadiazol-2-yl]-carbamoyl]- | 208 |
| 4 | (structure) | Coumarin, 7-chloro-4-hydroxy-3-[N-[5-bromo-1,3,4-thiadiazol-2-yl]-carbamoyl]- | 327 |

TABLE 1-continued

Increase of Insulin Receptor Autophosphorylation

| Compound No. | Structure | Compound Name | % of 2 nM insulin response |
|---|---|---|---|
| 5 | | Coumarin, 6-fluoro-4-hydroxy-3-[N-[5-(trifluoromethyl)-1,3,4-thiadiazol-2-yl]-carbamoyl]- | 180 |
| 6 | | Coumarin, 4-hydroxy-7-nitro-3-[N-(4-bromophenyl)-carbamoyl]- | 162 |
| 7 | | Coumarin, 4-hydroxy-5-methyl-3-[N-(4-bromophenyl)-carbamoyl]- | 210 |
| 8 | | Coumarin, 5-chloro-4-hydroxy-3-[N-(4-bromophenyl)-carbamoyl]- | 168 |
| 9 | | Coumarin, 5-chloro-4-hydroxy-3-[N-[5-(trifluoromethyl)-1,3,4-thiadiazol-2-yl]-carbamoyl]- | 224 |
| 10 | | Coumarin, 7-fluoro-4-hydroxy-3-[N-[5-(trifluoromethyl)-1,3,4-thiadiazol-2-yl]-carbamoyl]- | 196 |
| 11 | | Coumarin, 4-hydroxy-3-[N-(4-fluorophenyl)-carbamoyl]- | 201 |
| 12 | | Coumarin, 7-chloro-4-hydroxy-3-[N-[5-(chlorodifluoromethyl)-1,3,4-thiadiazol-2-yl]-carbamoyl]- | 314 |
| 13 | | Coumarin, 3-[N-(3-carbamoyl-5-methylthien-2-yl)carbamoyl]-4-hydroxy- | 166 |

TABLE 1-continued

Increase of Insulin Receptor Autophosphorylation

| Compound No. | Structure | Compound Name | % of 2 nM insulin response |
|---|---|---|---|
| 14 | | Coumarin, 4-hydroxy-3-[N-[5-chloro-1,3,4-thiadiazol-2-yl]-carbamoyl]- | 152 |
| 15 | | Coumarin, 7-chloro-4-hydroxy-3-[N-[5-chloro-1,3,4-thiadiazol-2-yl]-carbamoyl]- | 279 |
| 16 | | Coumarin, 7-chloro-4-hydroxy-3-[N-[5-(difluoromethyl)-1,3,4-thiadiazol-2-yl]-carbamoyl]- | 337 |
| 17 | | Coumarin, 4-hydroxy-3-[N-(3-chloro-5-(trifluoromethyl)-pyridin-2-yl)carbamoyl]- | 185 |
| 18 | | Coumarin, 7-chloro-4-hydroxy-3-[N-[5-(trifluoromethyl)-1,3,4-triazol-2-yl]carbamoyl]- | 161 |
| 19 | | Coumarin, 7-chloro-4-hydroxy-3-[N-[4-(1-(diethylphosphonyl)-ethyl)phenyl]-carbamoyl]- | 161 |
| 20 | | Coumarin, 4-hydroxy-3-[N-(4-(5-(trifluoromethyl)-1,3,4-thiadiazol-2-yloxy)phenyl)-carbamoyl]- | 165 |
| 21 | | Coumarin, 7-chloro-4-hydroxy-3-[N-(4-benzoyl-phenyl)carbamoyl]- | 171 |

TABLE 1-continued

Increase of Insulin Receptor Autophosphorylation

| Compound No. | Structure | Compound Name | % of 2 nM insulin response |
|---|---|---|---|
| 22 | | Coumarin, 4-hydroxy-7-phenoxy-3-[N-[5-(trifluoromethyl)-1,3,4-thiadiazol-2-yl]-carbamoyl]- | 190 |
| 23 | | Coumarin, 7-chloro-4-hydroxy-3-[N-(2-chlorophenyl)carbamoyl]- | 200 |
| 24 | | Coumarin, 6,7-dichloro-4-hydroxy-3-[N-(4-bromophenyl)-carbamoyl]- | 151 |
| 25 | | Coumarin, 4-hydroxy-7-trifluoromethyl-3-{N-[5-(trifluoromethyl)-1,3,4-thiadiazol-2-yl]-carbamoyl]- | 260 |
| 26 | | Coumarin, 4-hydroxy-7-trifluoromethyl-3-{n-{5-(pentafluoroethyl)-1,3,4-thiadiazol-2-yl]-carbamoyl] | 196 |
| 27 | | Coumarin, 7-bromo-4-hydroxy-3-[N-[5-(chlorodifluoromethyl)-1,3,4-thiadiazol-2-yl]-carbamoyl]- | 267 |
| 28 | | Coumarin, 7-bromo-4-hydroxy-3-[N-[5-(chlorodifluoromethyl)-1,3,4-thiadiazol-2-yl]-carbamoyl]- | 267 |
| 29 | | Coumarin, 6-chloro-4-hydroxy-3-[N-[5-(trifluoromethyl)-1,3,4-thiadiazole-2-yl]-carbamoyl]- | 222 |

TABLE 1-continued

Increase of Insulin Receptor Autophosphorylation

| Compound No. | Structure | Compound Name | % of 2 nM insulin response |
|---|---|---|---|
| 30 | | Coumarin, 7-trifluoromethyl-4-hydroxy-3-[N-[5-(difluorochloromethyl)-1,3,4-thiadiazole-2-yl]-carbamoyl]- | 251 |
| 31 | | Coumarin, 7-fluoro-4-hydroxy-3-[N-[5-(difluoromethyl)-1,3,4-thiadiazole-2-yl]-carbamoyl]- | 229 |
| 32 | | Coumarin, 7-trifluoromethyl-4-hydroxy-3-[N-[5-(difluoromethyl)-1,3,4-thiadiazole-2-yl]-carbamoyl]- | 208 |
| 33 | | Coumarin 7-fluoro-4-hydroxy-3-[N-[5-(difluorochloromethyl)-1,3,4-thiadiazole-2-yl]-carbamoyl]- | 246 |
| 34 | | Coumarin, 7-chloro-4-hydroxy-3-[N-[5-(aminosulfonyl)-1,3,4-thiadiazole-2-yl]carbamoyl]- | 172 |
| 35 | | Coumarin, 7-chloro-4-hydroxy-3-[N-[5-(dimethylaminosulfonyl)-1,3,4-thiadiazole-2-yl]carbamoyl]- | 274 |
| 36 | | 3H-Naptho[2,1-b]pyran-3-one, 1-hydroxy-2-[N-[5-(trifluoromethyl)-1,3,4-thiadiazole-2-yl]carbamoyl]- | 161 |
| 37 | | Coumarin, 5-fluoro-4-hydroxy-3-[N-[5-(trifluoromethyl)-1,3,4-thiadiazole-2-yl]-carbamoyl]- | 191 |
| 38 | | Coumarin, 5-fluoro-4-hydroxy-3-[N-[5-(difluoromethyl)-1,3,4,-thiadiazole-2-yl]-carbamoyl- | 238 |

TABLE 1-continued

Increase of Insulin Receptor Autophosphorylation

| Compound No. | Structure | Compound Name | % of 2 nM insulin response |
|---|---|---|---|
| 39 | | Coumarin, 6-fluoro-4-hydroxy-3-[N-[5-(difluoromethyl)-1,3,4-thiadiazole-2-yl]-carbamoyl]- | 186 |
| 40 | | Coumarin, 5-fluoro-4-hydroxy-3-[N-[5-(pentafluoroethyl)-1,3,4-thiadiazole-2-yl]-carbamoyl]- | 179 |
| 41 | | Coumarin, 5-fluoro-4-hydroxy-3-[N-[5-(difluorochloromethyl)-1,3,4-thiadiazole-2-yl]carbamoyl]- | 218 |
| 42 | | Coumarin, 6-bromo-4-hydroxy-3-[N-[5-(difluorochloromethyl)-1,3,4-thiadiazole-2-yl]-carbamoyl]- | 210 |
| 43 | | Coumarin, 6-chloro-4-hydroxy-3-[N-[5-(difluoromethyl)-1,3,4-thiadiazole-2-yl]-carbamoyl]- | 180 |

We claim:

1. A method of treating a patient suffering from or susceptible to diabetes mellitus comprising the administration of an effective mount of a compound of formula I or pharmaceutical acceptable salts thereof wherein:

$R_1$ is
(a) H,
(b) F,
(c) Cl, or
(d) $CH_3$;

$R_2$ is
(a) H,
(b) F,
(c) Cl,
(d) Br, or
(e) Phenyl;
or $R_1$ and $R_2$ taken together is phenyl;

$R_3$ is
(a) H,
(b) Cl,
(c) F,
(d) $-NO_2$,
(e) phenoxy,
(f) Br, or
(g) $CF_3$;

$R_4$ is
(a) 3-carbamoyl-5-methylthien-2-yl,
(b) 5-(trifluoromethyl)-1,3,4-triazol, R₅ is
 (a) H, or
 (b) Cl;

R₆ is
 (a) H,
 (b) Br,
 (c) F,
 (d) benzoyl,
 (e) 5-trifluoromethyl-1,3,4-thiadiazol-2-oxy, or
 (f) (CH₃)CH—P—O(OEt₂);

R₇ is
 (a) —SO₂CH₃,
 —SO₂NH₂,
 (c) —SO₂N(CH₃)₂,
 (d) CF₃,
 (e) CF₂Cl,
 (f) CF₂H,
 (g) Br,
 (h) Cl, or
 (i) CF₂CF₃;

R₈ is
 (a) H, or
 (b) Cl; and

R₉ is
 (a) Br, or
 (b) CF₃.

2. A method according to claim 1 whereto said compound of the formula I is administered orally, parenterally, or topically in a pharmaceutical composition.

3. A method according to claim 1 wherein said compound of the formula I is administered orally in a pharmaceutical composition.

4. A method according to claim 1 whereto said effective amount of the compound of the formula I ranges from 0.1–100 mg/kg of body weight/day.

5. A method according to claim 1 whereto said effective amount of the compound of the formula I ranges from 0.1–50 mg/kg of body weight/day.

6. A method according to claim 1 whereto said diabetic mellitus is insulin dependent diabetes mellitus.

7. A method according to claim 1 wherein said diabetic mellitus is non-insulin dependent diabetes mellitus.

8. A method according to claim 1 wherein said compound of the formula I is:

(a) Coumarin, 4-hydroxy-6-phenyl-3-[N-(5-bromopyridin-2-yl)carbamoyl]-;
(b) Coumarin, 7-chloro-4-hydroxy-3-[N-[5-(methylsulfonyl)-1,3,4-thiadiazol-2-yl]carbamoyl]-;
(c) Coumarin, 7-chloro-4-hydroxy-3-[N-[5-(trifluoromethyl)-1,3,4-thiadiazol-2-yl]carbamoyl]-;
(d) Coumarin, 3-[N-(3-carbamoyl-5-methylthien-2-yl) carbamoyl]-4-hydroxy-;
(e) Coumarin, 6-fluoro-4-hydroxy-3-[N-[5-(trifluoromethyl)-1,3,4-thiadiazol-2-yl]carbamoyl]-;
(f) Coumarin, 4-hydroxy-7-nitro-3-[N-(4-bromophenyl) carbamoyl]-;
(g) Coumarin, 4-hydroxy-5-methyl-3-[N-(4-bromophenyl)carbamoyl]-;
(h) Coumarin, 5-chloro-4-hydroxy-3-[N-(4-bromophenyl)carbamoyl]-;
(i) Coumarin, 5-chloro-4-hydroxy-3-[N-[5-(trifluoromethyl)-1,3,4-thiadiazol-2-yl]carbamoyl]-;
(j) Coumarin, 7-fluoro-4-hydroxy-3-[N-[5-(trifluoromethyl)-1,3,4-thiadiazol-2-yl]carbamoyl]-;
(k) Coumarin, 4-hydroxy-3-[N-(4-fluorophenyl) carbamoyl]-;
(l) Coumarin, 7-chloro-4-hydroxy-3-[N-[5-(chlorodifluoromethyl)-1,3,4-thiadiazol-2-yl] carbamoyl]-;
(m) Coumarin, 7-chloro-4-hydroxy-3-[N-[5-bromo-1,3,4-thiadiazol-2-yl]carbamoyl]-;
(n) Coumarin, 4-hydroxy-3-[N-[5-chloro-1,3,4-thiadiazol-2-yl]carbamoyl]-;
(o) Coumarin, 7-chloro-4-hydroxy-3-[N-[5-chloro-1,3,4-thiadiazol-2-yl]carbamoyl]-;
(p) Coumarin, 7-chloro-4-hydroxy-3-[N-[5-(difluoromethyl)-1,3,4-thiadiazol-2-yl]carbamoyl]-;
(q) Coumarin, 4-hydroxy-3-[N-(3-chloro-5-(trifluoromethyl)-pyridin-2-yl)carbamoyl]-;
(r) Coumarin, 7-chloro-4-hydroxy-3-[N-[5-(trifluoromethyl)-1,3,4-triazol-2-yl]carbamoyl]-;
(s) Coumarin, 7-chloro-4-hydroxy-3-[N-[4-(1-(diethylphosphonyl)ethyl)-phenyl]carbamoyl]-;
(t) Coumarin, 4-hydroxy-3-[N-(4-(5-(trifluoromethyl)-1,3,4-thiadiazol-2-yloxy)phenyl)carbamoyl]-;
(u) Coumarin, 7-chloro-4-hydroxy-3-[N-(4-benzoylphenyl)carbamoyl]-;
(v) Coumarin, 4-hydroxy-7-phenoxy-3-[N-[5-(trifluoromethyl)-1,3,4-thiadiazol-2-yl]carbamoyl]-;
(w) Coumarin, 7-chloro-4-hydroxy-3-[N-(2-chlorophenyl)carbamoyl]-;
(x) Coumarin, 6,7-dichloro-4-hydroxy-3-[N-(4-bromophenyl)carbamoyl]-,
(y) Coumarin, 4-hydroxy-7-trifluoromethyl-3-[N-[5-(trifluoromethyl)-1,3,4-thiadiazol-2-yl]carbamoyl]-;
(z) Coumarin, 4-hydroxy-7-trifluoromethyl-3-[N-[5-(pentafluoroethyl)-1,3,4-thiadiazol-2-yl]carbamoyl]-;
(aa) Coumarin, 7-bromo-4-hydroxy-3-[N-[5-(chlorodifluoromethyl)-1,3,4-thiadiazol-2-yl] carbamoyl]-;
(bb) Coumarin, 7-bromo-4-hydroxy-3-[N-[5-(difluoromethyl)-1,3,4-thiadiazol-2-yl]carbamoyl]-;
(cc) Coumarin, 6-chloro-4-hydroxy-3-[N-[5-(trifluoromethyl-1,3,4-thiadiazole-2-yl]carbamoyl]-;
(dd) Coumarin, 7-trifluoromethyl-4-hydroxy-3-[N-[5-(difluorochloromethyl)-1,3,4-thiadiazole-2-yl] carbamoyl]-;
(ee) Coumarin, 7-fluoro-4-hydroxy-3-[N-[5-(difluoromethyl)-1,3,4-thiadiazole-2-yl]carbamoyl]-;
(ff) Coumarin, 7-trifluoromethyl-4-hydroxy-3-[N-[5-(difluoromethyl)-1,3,4-thiadiazole-2-yl]carbamoyl]-;
(gg) Coumarin, 7-fluoro-4-hydroxy-3-[N-[5-(difluorochloromethyl)-1,3,4-thiadiazole-2-yl] carbamoyl]-;
(hh) Coumarin, 7-chloro-4-hydroxy-3-[N-[5-(aminosulfonyl)-1,3,4-thiadiazole-2-yl]carbamoyl]-;
(ii) Coumarin, 7-chloro-4-hydroxy-3-[N-[5-(dimethylaminosulfonyl)-1,3,4-thiadiazole-2-yl] carbamoyl]-;

(jj) 3H-Naptho[2,1-b]pyran-3-one, 1-hydroxy-2-[N-[5-(trifluoromethyl)-1,3,4-thiadiazole-2-yl]carbamoyl]-;

(kk) Coumarin, 5-fluoro-4-hydroxy-3-[N-[5-(trifluoromethyl)-1,3,4-thiadiazole-2-yl]carbamoyl]-;

(ll) Coumarin, 5-fluoro-4-hydroxy-3-[N-[5-(difluoromethyl)-1,3,4-thiadiazole-2-yl]carbamoyl]-;

(mm) Coumarin, 6-fluoro-4-hydroxy-3-[N-[5-(difluoromethyl)-1,3,4-thiadiazole-2-yl]carbamoyl]-;

(nn) Coumarin, 5-fluoro-4-hydroxy-3-[N-[5-(pentafluoroethyl)-1,3,4-thiadiazole-2-yl]carbamoyl]-;

(oo) Coumarin, 5-fluoro-4-hydroxy-3-[N-[5-(difluorochloromethyl)-1,3,4-thiadiazole-2-yl]carbamoyl]-;

(pp) Coumarin, 6-bromo-4-hydroxy-3-[N-[5-(difluorochloromethyl)-1,3,4-thiadiazole-2-yl]carbamoyl]-; or (qq) Coumarin, 6-chloro-4-hydroxy-3-[N-[5-(difluoromethyl)-1,3,4-thiadiazole-2-yl]carbamoyl]-.

\* \* \* \* \*